US00PP13272P3

(12) United States Plant Patent
Olesen et al.

(10) Patent No.: US PP13,272 P3
(45) Date of Patent: Nov. 26, 2002

(54) COMPACT FLORIBUNDA ROSE PLANT NAMED 'POULAC001'

(76) Inventors: L. Pernille Olesen, Hillerødvejen 49, DK-3480 Fredensborg (DK); Mogens N. Olesen, Hillerødvejen 49, DK-3480, Fredensborg (DK)

( * ) Notice: Subject to any disclaimer, the term of this patent is extended or adjusted under 35 U.S.C. 154(b) by 0 days.

(21) Appl. No.: 09/776,157

(22) Filed: Feb. 2, 2001

(65) Prior Publication Data

US 2002/0148015 P1 Oct. 10, 2002

(51) Int. Cl.[7] ..... A01H 5/00
(52) U.S. Cl. ..... Plt./148
(58) Field of Search ..... Plt./148, 141, 102

*Primary Examiner*—Bruce R. Campell
*Assistant Examiner*—June Hwu

(57) ABSTRACT

A new compact floribunda rose which has abundant, light pink flowers and attractive foliage. This new and distinct variety has shown to be uniform and stable in the resulting generations from asexual propagation.

1 Drawing Sheet

BOTANICAL CLASSIFICATION

*Rosa hybrida* 'POULac001'.

SUMMARY OF THE INVENTION

The present invention constitutes a new and distinct variety of floribunda rose plant which originated from a controlled crossing between 'POULfiry' described and illustrated in U.S. Plant Pat. No. 12,484, dated Mar. 26, 2002 and 'POULsint' an unpatented variety. The two parents were crossed during the summer of 1996 and the resulting seeds were planted in a controlled environment in Fredensborg, Denmark. The new variety is named 'POULac001'.

The new rose may be distinguished from its seed parent, 'POULfiry', by the following combination of characteristics:

1. 'POULac001' has pink flowers, while 'POULfiry' has bright orange flowers.
2. 'POULac001', as a compact floribunda is taller in habit when compared to the miniature rose 'POULfiry'.
3. 'POULfiry' exhibits more anthocyanin in the foliage when compared to 'POULac001'.

The new variety may be distinguished from its pollen parent, 'POULsint' by the following combination of characteristics:

1. 'POULac001' exhibits light pink flowers, whereas the pollen parent exhibits orange-red flowers.
2. 'POULac001' has a larger flower diameter than that of 'POULsint'.
3. 'POULac001' has glossy foliage, whereas 'POULsint' displays matte foliage.

The objective of the hybridization of this rose variety was to create a new and distinct variety for garden use with unique qualities, such as:

1. Uniform and abundant pink flowers;
2. Vigorous, but compact growth when propagated both as a budded rose and on its own roots;
3. Disease resistance.
4. Suitability for production in pots.

This combination of qualities is not present in previously available commercial cultivars of this type and distinguish 'POULac001' from all other varieties of which we are aware.

As part of their rose development program, L. Pernille Olesen and Mogens N. Olesen germinated the seeds from the aforementioned hybridization during winter 1996 and conducted evaluations on the resulting seedlings in a controlled environment in Fredensborg, Denmark.

'POULac001' was selected in the spring 1997 by the inventors as a single plant from the progeny of the aforementioned hybridization. Asexual reproduction of 'POULac001' by traditional budding and rooted cuttings was first done by L. Pernille and Mogens N. Olesen in their nursery in Fredensborg, Denmark in July 1997. This initial and other subsequent asexual propagations conducted in controlled environments have demonstrated that the characteristics of 'POULac001' are true to type and are transmitted from one generation to the next.

BRIEF DESCRIPTION OF THE DRAWING

The accompanying color illustration shows as true as is reasonably possible to obtain in color photographs of this type the variety rose 'POULac001'.

Specifically illustrated in SHEET 1 include:

1. Rose plant exhibiting foliage, leaves, and leaflets.
2. Flower bud, partially opened bud, and open bloom;
3. General plant growth and habit.

DETAILED DESCRIPTION OF THE VARIETY

The following is a description of 'POULac001' as observed in its growth in a nursery in Jackson County, Oreg., on plants aged eighteen weeks. Color references are made using The Royal Horticultural Society (London, England) Colour Chart, 1995, except where common terms of color are used.

For a comparison, several physical characteristics of the rose variety 'POULskov', a rose variety from the same inventors described and illustrated in U.S. Plant Pat. No. 9,062 and issued on Feb. 28, 1995 are compared to 'POULac001' in Chart 1.

CHART 1

| | 'POULac001' | 'POULskov' |
|---|---|---|
| Color of open flower, outer side, middle zone. | Red Group 55B | Red Group 56B–56D |
| Petalage | Double, 25+ | Very double 50–60 petals |
| Flower size | 8–10 cm | 6–8 cm |

Classification:
*Commercial.*—Compact floribunda.
Parents:
*Seed parent.*—'POULfiry'.
*Pollen parent.*—'POULsint'.

FLOWER AND FLOWER BUD

Blooming habit: Continuous.
Flower bud:
*Size.*—32 to 34 mm in length from base of receptacle to end of bud.
*Bud form.*—Ovate.
*Bud color.*—As sepals unfold, Red Group 54B. Red Group 54B and C at ¼ opening.
*Sepals.*—Length: 25 mm. Width: 8 mm. Coloration of upper surface is Yellow-Green Group 146B at margins and Yellow-Green Group 146C in middle and basal zones. Lower surface is Yellow-Green Group 146C. Anthocyanin occasionally present on upper surface sepals, Greyed-Red Group 182A. Shape: Sepal apex is cirrose; base is flat at union with peduncle.
*Receptacle.*—Surface: Smooth. Shape: Funnel shaped. Size: 6 mm wide and 6 mm high. Color: Green Group 143C.
*Peduncle.*—Surface: Moderate quantity of stipitate glands present. Length: 25 to 30 mm. Color: Yellow-Green Group 146C. Strength: Strong. Anthocyanin: Greyed-Red Group 181B.
*Borne.*—1 to 5 flowering shoots per stem.
Flower bloom:
*Fragrance.*—Weak.
*Size.*—Medium. Average flower diameter is between 8–10 cm when open.
*Duration.*—Blooms last from 6 to 8 days; petals fall cleanly.
*Form.*—Shape of flower when viewed from the side: Upon opening, upper part: Concave. Upon opening, lower part: Flattened convex. Open flower, upper part: Concave. Open flower, lower part: Flattened convex. Petalage: Double. Average range: 25 petals under normal conditions, with 3 to 5 petaloids.
Color:
*Upon opening, petals.*—Outermost petals: Upper surface: Red Group 54B. Lower surface: Red Group 54C with intonations of Red Group 54B. Innermost petals: Upper surface: Red Group 52D. Lower surface: Red Group 49A.
*Upon opening, basal petal spots.*—Upper surface: Yellow Group 8B. Lower surface: Yellow Group 8C.
*After opening, petals.*—Outermost petals: Upper surface: Red Group 54C, with intonations of Red Group 54B. Lower surface: Red Group 55D. Innermost petals: Upper surface: Red Group 54B. Lower surface: Red Group 54C.
*After opening, basal petal spots.*—Upper surface: Yellow Group 8B. Lower surface: Yellow Group 8B.
General Tonality: On open flower, Red Group 55C. No change in the general tonality at the end of the $7^{th}$ day. Afterwards, general tonality is Red Group 55D.
Petals:
*Petal reflex.*—Strong.
*Petal edge.*—Ruffled.
*Shape.*—Obovate.
*Petaloids.*—3 to 5. Petaloids are 20 to 25 mm long and 10 to 15 mm wide. Petaloid coloration is Red Group 55C on upper surface and Red Group 55 A and B on lower surface.
*Thickness.*—Moderately thick.
*Size.*—20 mm (l)×15 mm (w).
Reproductive organs:
*Pistils.*—Length: 8 mm. Quantity: Approximately 40.
*Pollen.*—None observed.
*Anthers.*—Length: 2 mm. Color: Margins are Greyed-Orange Group 163A. Interior is Greyed-Orange Group 163C. Quantity: 100.
*Filaments.*—Color: Yellow Group 12A. Length: 5 to 6 mm.
*Stigmas.*—Slightly superior in position relative to anthers. Color is Yellow-Green Group 150D.
*Styles.*—Color: Yellow-Green Group 150D, with intonations of Greyed-Purple Group 184C.
*Hips.*—None observed.

PLANT

Plant growth: Dense, compact, and even growth. When grown as 15-cm pot plant the average height of the plant is 40 cm and the average width is 60 cm.
Stems:
*Color.*—Young wood: Yellow-Green Group 146C. Older wood: Yellow-Green Group 146C.
*Texture.*—Young wood: Smooth. Older wood: Smooth.
*Thorns.*—Incidence: 12 thorns per 10 cm of stem. Size: Average length is 5 mm. Color: Greyed-Orange Group 174 A and B. Shape: Concave.
Plant foliage:
*Typical number of leaflets on leaves in the middle of stem.*—5.
*Leaf size.*—95 mm long and 60 to 65 mm wide.
*Quantity.*—Average.
*Glossy.*—Upper side weak glossiness.
*Color mature foliage.*—Upper Leaf Surface: Yellow-Green Group 146A. Lower Leaf Surface: Yellow-Green Group 146C.
*Color, juvenile foliage.*—Upper Leaf Surface: Yellow-Green Group 146A. Lower Leaf Surface: Yellow-Green Group 146C. Anthocyanin intonation: Greyed-Purple Group 184A. Present on new growth, on stems, upper and lower leaflet margins, rachii, and stipules.
Plant leaflets:
*Stipules.*—Size: 15 to 16 mm long. Color: Margins are Yellow-Green Group 146A; interior is Yellow-Green Group 146D. Stipitate Glands: Present on stipule margins. Anthocyanin: Greyed-Purple Group 184A.
*Petiole.*—Length: 4 to 8 mm. Color: Yellow-Green Group 146C. Underside: Occasional small thorn present. Anthocyanin: Greyed-Purple Group 184A.
*Rachis.*—Color: Yellow-Green Group 146C. Underside: Occasional small thorn present. Margins: With stipitate glands. Anthocyanin: Greyed-Purple Group 184A.
*Leaflet.*—Edge: Serrated. Shape: Broadly ovate. Apex Shape: Cirrose. Glossiness: Moderate. Texture:

Thick. Arrangement: Odd pinnate. Venation: Reticulate.

Disease resistance: Above average resistance to mildew, rust, black spot, and Botrytis under normal growing conditions in Fredensborg, Denmark and Hannover, Germany.

Cold hardiness: The variety 'POULac001' has been found to be cold hardy in Fredensborg, Denmark and Hannover, Germany.

We claim:

1. A new and distinct variety of rose plant of the compact floribunda rose class, substantially as herein illustrated and described as a distinct and novel rose variety due to its abundant light pink flowers, disease resistance, and extended period of bloom.

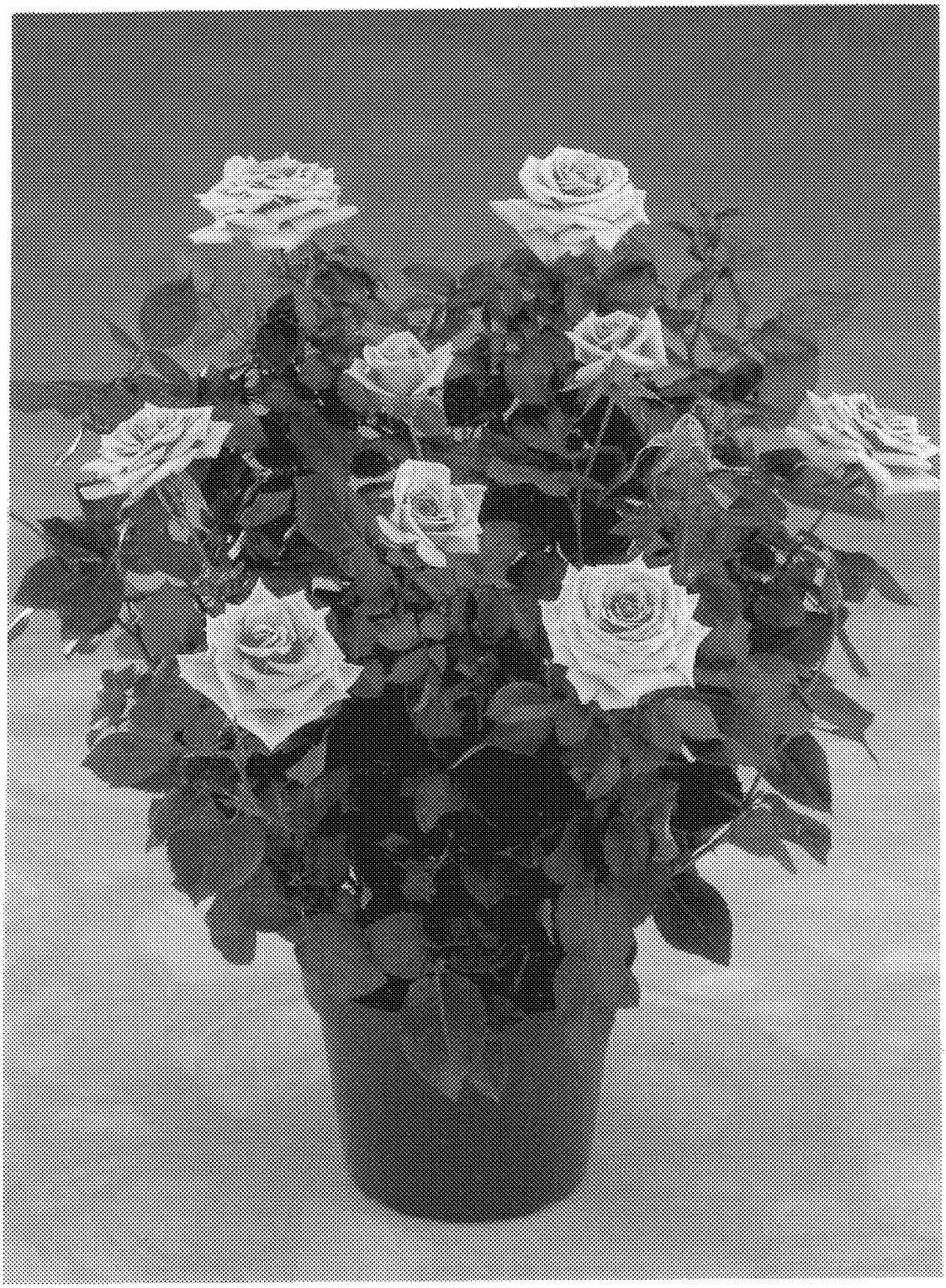

* * * * *